United States Patent [19]

Ullman et al.

[11] 4,193,983

[45] Mar. 18, 1980

[54] LABELED LIPOSOME PARTICLE COMPOSITIONS AND IMMUNOASSAYS THEREWITH

[75] Inventors: Edwin F. Ullman, Atherton; John M. Brinkley, Oakland, both of Calif.

[73] Assignee: Syva Company, Palo Alto, Calif.

[21] Appl. No.: 906,514

[22] Filed: May 16, 1978

[51] Int. Cl.² .................... G01N 31/00; G01N 33/16; G01N 23/00; A61K 37/00

[52] U.S. Cl. .................................. 424/12; 23/230 B; 260/112 R; 260/112 B; 424/1; 424/3; 424/7; 424/8; 424/11; 424/13; 424/38; 435/7; 435/188

[58] Field of Search ........................ 424/1, 3, 7, 8, 11, 424/12, 13, 38; 260/112 R, 112 B; 23/230 B; 195/103.5 A, 103.5 L, 63

[56] References Cited

U.S. PATENT DOCUMENTS

| | | | |
|---|---|---|---|
| 3,849,546 | 11/1974 | Beaumont | 424/13 X |
| 3,882,224 | 5/1975 | Forgione | 424/11 X |
| 3,887,698 | 6/1975 | McConnell | 424/13 X |
| 3,949,065 | 4/1976 | Forgione | 424/13 X |
| 3,996,345 | 12/1976 | Ullman | 424/8 |
| 4,104,029 | 8/1978 | Maier | 424/8 X |

OTHER PUBLICATIONS

Sato, Japan J. Exp. Med., vol. 46, 1976, pp. 213–221.
Schwenk, The J. of Immunology, vol. 120, No. 5, May 1978, pp. 1612–1615.

*Primary Examiner*—Anna P. Fagelson
*Attorney, Agent, or Firm*—Bertram I. Rowland

[57] ABSTRACT

The subject invention concerns novel compositions for use in immunoassays, as well as immunoassays employing such novel compositions. The compositions comprise discrete charged colloidal particles comprised of small molecules which particles are capable of retaining their discrete character in an aqueous medium and composed of aggregates of lipophilic and/or amphiphilic organic molecules to which are bound non-covalently a label capable of producing a detectible signal and a ligand or an analog of the ligand capable of competing with a ligand for a ligand receptor. The discrete colloidal particle serves as a hub or nucleus for retaining the ligand or its analog and the label within a limited locus.

The compositions are prepared by individually covalently bonding the ligand and the label, when not naturally lipophilic, to a lipophilic (includes amphiphilic) compound, normally a phospholipid. Depending upon the nature of the particle, the amphiphilic conjugated ligand and label are combined with the particle or alternatively may be combined with the compounds employed for preparing the particle under particle forming conditions. Particles are then obtained having the analog of the ligand and the label bound to the particle.

The compositions find use in immunoassays where an interaction between the label and receptor provides a means for modulating a detectible signal. The interaction can be as a result of quenching or modification of fluorescence, where the label is a fluorescer, steric inhibition of the approach of a signal modifier to the label, such as a label receptor or with an enzyme label, an antienzyme or enzyme inhibitor, the inhibition of cleavage of an enzyme labile bond or the cooperative interaction of two labels, such as two enzymes, where the product of one enzyme is a substrate of another enzyme.

17 Claims, No Drawings

LABELED LIPOSOME PARTICLE COMPOSITIONS AND IMMUNOASSAYS THEREWITH

BACKGROUND OF THE INVENTION

1. Field of the Invention

Protein binding assays have become of increasing importance in the diagnosing of diseased states, the monitoring of the administration of drugs, and the determination of trace amounts of organic compounds unrelated to human health. Protein binding assays are particularly applicable in the determination of specific compounds which are present at concentrations of $10^{-6}$ M or less, particularly where they are present in a mixture of other compounds having similar properties.

Protein binding assays depend upon the ability of labeling an analyte, where the label provides a detectible signal, and where binding of the receptor to the labeled analyte permits discrimination between bound and unbound label. The presence of the receptor can either allow for a mechanical separation of bound and unbound labeled analyte or can affect the label in such a way as to modulate the detectible signal. The former situation is normally referred to as heterogeneous and the latter as homogeneous, in that the latter technique avoids a separation step.

In developing protein binding assays, there are a number of considerations. Considerations related to the choice of label include the sensitivity it provides, synthetic problems, stability, its sensitivity to changes in environment and the like. Other considerations are the purity required for the analyte and/or analyte receptor in preparing the reagents and in the assay. Additional considerations are the effect of varying analyte on the synthetic procedures, the properties of the label, and the sensitivity and accuracy of the assay. By having an assay technique which is generally applicable to a wide variety of analytes and is not significantly affected by variation in analyte, the preparation of reagents and the performance of the assay can be readily adapted to new and varying analytes.

2. Description of the Prior Art

Badley, "Fluorescent Probing of Dynamic and Molecular Organization of Biological Membranes," Modern Fluorescence Spectroscopy, Vol. 2 Ed. E. L. Wehry, Plenum Press, N.Y. 1976 and Kanaoka, Angew. Chem. Int. Ed. Engl. 16, 137 (1977) discuss fluorescent probes in biological systems. Wu et al, Biochemistry, 16, 3936 (1977), Harris, Chemistry and Physics of Lipids 19, 243 (1977) Smolarsky et al, J. of Imm. Meth., 15, 255 (1977) and Waggoner and Stryer, Proc. Nat. Acad. Sci. 67, 579 (1970) describe the use of fluorescent probes with biological membranes. Uemura, et al, Biochemistry 13, 1572 (1974), Alving and Richards, Immunochemistry 14, 373 (1977), Geiger and Smolarsky, J. Imm. Meth., 17, 7 (1977), Inoue and Nojima, Chem. Pharm. Bull. 16, 76 (1968) and Tamamura, et al, Japan J. Exp. Metd. 41, 31 (1971) describe antibody phospholipid interactions.

U.S. Pat. Nos. 3,850,578 and 3,887,698, and the references cited therein, teach the use of liposomes in assays where complement mediated lysis of the liposome as a result of antibody binding to an antigen bound to the liposome results in release of stable free radicals contained in the liposome.

SUMMARY OF THE INVENTION

Novel compositions are provided which find use in homogeneous protein binding assays, which compositions are discrete colloidal particles substituted with at least one label and at least one ligand. The particles are formed with small lipophilic (includes amphiphilic) molecules and the label and ligand are joined to the particle non-covalently, but in a substantially fixed average spatial relationship. The particles may be vesicles, oil droplets or the like, having an ordered surface layer bearing a net electrostatic charge.

The particles are formed by combining in an aqueous medium the lipophilic particle forming molecules, either individually or as a particle, any auxiliary components, and the lipophilic conjugates, including the ligand conjugates, as the naturally occurring ligand or as a conjugate with a lipophilic compound, and the label conjugate.

The particles find use in protein binding assays where the presence of receptor bound to ligand adjacent the label can be used to modulate the signal provided by the label. Illustrative of such situations are assays where the presence of receptor inhibits the approach of another molecule to the label or the receptor is conjugated with a molecule which interacts with the label to modulate the signal.

DESCRIPTION OF THE SPECIFIC EMBODIMENTS

Novel compositions are provided which find use in the performance of protein binding assays. The compositions employ a colloidal particle as hub or nucleus for controlling a spatial relationship between a label and a ligand, where the label and ligand are non-covalently bound to the central nucleus. The central nucleus is a stable colloidal particle that consists of a discrete phase different from the aqueous solvent and is comprised of organic molecules, which are at least in part lipophilic. The particles are comprised of a hydrophilic normally electrostatically charged surface layer surrounding a hydrophobic layer or core. By employing ligands and labels which are naturally lipophilic or made so by conjugation with lipophilic compounds, both the label and the ligand become non-covalently bound to the discrete particle. By providing for appropriate amounts of the label and ligand, a substantial proportion of the label and ligand will be in relatively close spatial proximity on the surface of the particle.

In protein binding assays, the ligand of interest is normally labeled and the assay allows for discrimination between the amount of labeled ligand which is bound to receptor and the amount of labeled ligand which is unbound. In heterogeneous assays, the discrimination is a result of physical separation. In homogeneous assays, the discrimination is a result of modulation of the signal provided by the label. By virtue of having the label and ligand in relatively close proximity on the surface of the particle, the proximity of the label and the receptor bound to the ligand adjacent the label can be used in accordance with the prior art techniques to modulate the signal from the label.

By employing the subject invention, numerous advantages ensue. One advantage is that one has a simple hub nucleus to which a wide variety of labels and ligands may be easily bound in a relatively uniform manner and at a variety of ratios. Secondly, with large ligands, one can readily bond the relatively small lipophilic compound to the large ligand. Thirdly, one does not directly bond the label to the ligand. This can be very important where the ligand is not readily obtainable in pure form. Where the ligand is primarily obtainable as a complex mixture e.g. naturally occurring products, when labeling the ligand, one will also label the contaminant. The labeled contaminants will therefore provide a background which can seriously interfere with the sensitivity of the assay. In the subject invention since the ligand is indirectly labeled, there will be no labeled contaminants which interfere with the assay. Also, by preparing a single ligand lipophilic conjugate, one can employ this compound with a wide variety of labels. Similarly, one can prepare labels and employ them with a wide variety of ligands. In addition, for those ligands which require the presence of a liposome, the subject method inherently employs the necessary environment.

In order to enhance the understanding of the subject invention, a number of the terms which find repetitive usage will be defined.

Definitions

Analyte—the compound or composition to be measured, which may be a ligand which is mono- or polyepitopic, antigenic or haptenic, a single or plurality of compounds which share at least one common epitopic site or a receptor.

Ligand—any compound for which a receptor naturally exists or can be prepared.

Ligand Analog—a modified ligand which can compete with the analogous ligand for a receptor, the modification providing means to join a modified ligand to another molecule. The ligand analog will differ from the ligand by more than replacement of a hydrogen with a bond which serves to link the modified ligand to another molecule.

Receptor—any compound or composition capable of recognizing a particular spatial and polar organization of a molecule i.e. epitopic site. Illustrative receptors include naturally occurring receptors, antibodies, enzymes, Fab fragments, lectins, and the like. For any specific ligand, the receptor will be referred to as antiligand. For any specific label, the receptor will be referred to as antilabel. The receptor-antiligand- or antilabel and its homologous ligand or label form a specific binding pair.

Label—a compound which is either directly or indirectly involved with the production of a detectible signal and is bonded directly to one or more lipophilic molecules.

Illustrative labels include chromogens, e.g. fluorescers and chemiluminescers, catalysts, both enzymatic and non-enzymatic, molecules having an enzymatically labile bond which upon enzymatic cleavage provides a compound which can be detected, either directly or indirectly, and the like.

Conjugate—a conjugate intends the covalent bonding together of two molecules which serve different functions in the subject invention. The label-lipophile conjugate joins the label to one or more lipophiles. The ligand- or ligand analog-lipophile conjugate, hereinafter referred to as ligand-lipophile conjugate, joins the ligand or modified ligand to one or more lipophiles.

In some instances the label may be indirectly bound to the colloid particle. This can be achieved by employing a lipophilic compound, which includes conjugates of lipophilic groups with haptens and antigens, in the colloidal particle. Receptor e.g. antibodies and Fab fragments, which recognize or specifically bind to such lipophilic compound, including the haptenic or antigenic portion thereof, may be conjugated with label. The labeled receptor may then bind to the lipophilic compound in the colloidal particle indirectly labeling the particle. In this manner, the number of labels bound to the particle may be greatly enhanced.

Lipophile—For the most part are hydrocarbons or lipids. Lipids are amphipathic elongated molecules, much smaller in weight and size than polymers, but sufficiently large to have two distinct regions of greatly differing polarity. One is the polar (hydrophilic) region at one end of the molecule, which favors the interaction with water, and the other is the apolar (hydrophobic) region consisting of hydrocarbon chains. The amphipathic nature of the molecule is responsible for the molecular association phenomena characteristic of lipids in both crystals and lipid-water systems. See, Water, Volume 4, Aqueous Solutions of Amphiphiles and Macromolecules, Chapter 4, Lipids, page 213, Plenum Press, New York. See also, Tute, Chem. Ind. (London) 1975 (3), 100–5.

Amphiphile—see above definition of lipids. Amphiphiles may be neutral or charged: when negatively charged, usually having as the anionic group, phosphate, carboxylate, sulfonate or sulfate, particularly phosphate; when positively charged, usually having as the cationic group, ammonium e.g. pyridinium, tetralkyl ammonium, etc., phosphonium, or sulfonium, particularly ammonium.

Colloidal Particle—the colloidal particle is a small discrete particle capable of maintaining its integrity in an aqueous environment and comprised of lipophilic, usually amphiphilic, molecules. These particles may be considered as members of the class of association colloids, which are thermodynamically stable systems in which the dispersed phase consists of aggregates of molecules (or ions) of relatively small size and mass. See Remington's Pharmaceutical Sciences, 15th ed., Mack Publishing Co., Eastin, PA, 1975, page 300.

For the most part the colloidal particles will have regular shapes such as spheres, cylinders or plates. With amphiphilic molecules, the particle is composed of a hydrophilic, normally charged outer layer and a hydrophobic interior layer or core. The layer may be mono- or polylamellar and there may be an aqueous phase between layers. For lipophilic molecules, there will normally be a layer of amphiphilic molecules, usually charged, on the surface of the particle.

For the most part, the molecules will have molecular weights of at least about 150 and not greater than about 2,500, usually not greater than 1,500. The molecules will have at least twelve aliphatic carbon atoms (includes alicyclic), usually at least 18, and more usually at least 28 and usually not more than about 175 carbon atoms. The amphiphilic compounds will normally have an aliphatic chain of at least 10 carbon atoms, usually at least 12 carbon atoms and usually not more than about 36 carbon atoms, and will have from 0 to 3 sites of aliphatic unsaturation, usually ethylenic. The particles generally have a size of from about $2 \times 10^{-6}$ to $10^3 \mu^3$, more usually from about $6 \times 10^{-6}$ to $1 \mu^3$ and frequently from about $8 \times 10^{-6}$ to $10^{-3} \mu^3$. With liposomes, the membrane thickness will be about 50 to 100 Å.

In referring to particles prepared from lipophilic compounds other than amphiphilic compounds, these particles will be referred to as droplets. In referring to particles prepared from amphiphilic compounds, these particles will be referred to as vesicles or liposomes.

Colloidal particle reagent—the colloidal particle reagent is a colloidal particle which includes the label conjugate and the ligand or ligand conjugate (includes ligand analog conjugate) as part of the outer molecular layer, so that the ligand and label are confined to the particle surface in closer proximity than if randomly distributed in solution. The two conjugates or the label conjugate and amphipathic ligand are bound non-covalently to the particle by virtue of the presence of the lipophilic group.

Kit—a combination of reagents, usually formulated with ancillary reagents, such as buffer, salts, stabilizers, etc., where the reagents are premeasured so as to at least substantially optimize the assay sensitivity. Where the analyte is antiligand, the kit will comprise colloidal particle reagent and, as appropriate antilabel, modified or unmodified or modified antiligand. Where the analyte is ligand, the kit will comprise colloidal particle reagent, antiligand and as appropriate antilabel, with the receptors being modified or unmodified.

Modified receptor—receptor to which is conjugated a compound which interacts with the label to modulate the detectible signal. Illustrative compounds for receptor modification include chromogens which act as quenchers or energy receptors, enzymes or non-enzymatic catalysts.

Assay

The subject assay is carried out in an aqueous zone at a moderate pH, generally close to optimum assay sensitivity, normally without separation of the assay components or products. The assay zone for the determination of analyte is prepared by employing an appropriate aqueous solution, normally buffered, the unknown sample, which may have been subject to prior treatment, the colloidal particle reagent, any auxiliary materials associated with production of the detectible signal, as well as when appropriate, modified or unmodified receptor(s).

The presence of ligand or antiligand as the analyte in the unknown will affect the degree to which antiligand will bind to the colloidal particle reagent and influence the production of the detectible signal. In some instances, antiligand will be modified by having molecules bonded to it which interact with the label, and it is this interaction which modulates the detectible signal. In other instances, the proximity of the antiligand to the label without any modification of the antiligand will affect the detectible signal.

In carrying out the assay an aqueous medium will normally be employed. Other polar solvents may also be employed, usually oxygenated organic solvents of from 1-6, more usually from 1-4 carbon atoms, including alcohols, ethers and the like. Usually these cosolvents will be present in less than about 40 weight percent, more usually in less than about 20 weight percent.

The pH for the medium will usually be in the range of about 4-11, more usually in the range of about 5-10, and preferably in the range of about 6.5-9.5. The pH is chosen so as to maintain a significant level of specific binding by the receptor while optimizing signal producing proficiency. In some instances, a compromise will be made between these two considerations. Various buffers may be used to achieve the desired pH and maintain the pH during the determination. Illustrative buffers include borate, phosphate, carbonate, tris, barbital and the like. The particular buffer employed is not critical to this invention but in individual assays, one buffer may be preferred over another.

Moderate temperatures are normally employed for carrying out the assay and usually constant temperatures during the period of the assay. The temperatures for the determination will generally range from about 10°–50° C., more usually from about 15°–40° C.

The concentration of analyte which may be assayed will generally vary from about $10^{-4}$ to $10^{-15}$ M, more usually from about $10^{-6}$ to $10^{-13}$ M. Considerations such as whether the assay is qualitative, semi-quantitative or quantitative, the particular detection technique and the concentration of the analyte of interest will normally determine the concentrations of the other reagents.

While the concentrations of the various reagents will generally be determined by the concentration range of interest of the analyte, the final concentration of each of the reagents will normally be determined empirically to optimize the sensitivity of the assay over the range of interest.

The total binding sites of the member of the specific binding pair, which is reciprocal to the analyte, will be not less than about 0.1 times the minimum concentration of interest based on binding sites of the analyte and not more than about 1,000 times the maximum concentration of interest based on analyte binding sites, usually about 0.1–100 times, more usually about 0.1–10 times the maximum concentration of interest. Where receptor is the analyte and a modified receptor is employed as a reagent, the amount of modified receptor employed based on binding sites will be not less than about 0.01 times the minimum concentration of interest and usually not more than 100 times the maximum concentration of interest of the receptor. The auxiliary reagents employed with the label will be present in sufficient amount so as not to be rate controlling or interfere with the amount of signal as a function of analyte concentration. The amount will vary depending upon the nature of the label and the auxiliary reagents.

The order of addition of the various reagents may vary widely, depending upon the particular label, the nature of the analyte, and the relative concentrations of the analyte and reagents.

Also affecting the order of addition is whether an equilibrium mode or rate mode is employed for the determination.

In determining a particular order of addition, there will be certain basic considerations. Usually, the rate of association of receptor and ligand is much greater than the rate of dissociation, although this will be a factor not only of the binding constant, but also of the relative concentrations of the members of the specific binding pair. Another consideration is that one wishes to minimize the background, so that normally where a rate is measured, production of the signal will not be initiated prior to all of the components being present. Finally, the order of addition must not interfere with the ability of the analyte to affect the modulation of the detectible signal.

Where ligand is the analyte, the unknown sample may be combined with the ligand receptor and the resulting mixture combined with the colloidal particle reagent and any auxiliary reagents. Where receptor is the analyte, and a modified receptor is not employed as a reagent, the receptor may be simply added to the colloidal particle reagent, followed by the addition of auxiliary reagents. Where modified receptor is employed, the unknown sample and modified receptor may be combined and then added to the liquid particle reagent, again followed by the addition of auxiliary reagents. Alternatively, all of the primary reagents may be added simultaneously, concomitantly with or prior to the addition of the auxiliary reagents. One or more incubation steps may be involved, which will normally involve periods of from 0.1 min. to 6 hrs., more usually from about 1 min. to 1 hr., usually from about 5 min. to 30 min. Incubation temperatures will generally range from about 4° to 50° C., usually from about 15° to 37° C.

After the reagents are combined, the signal will then be determined. The method of determination may be the observation of electromagnetic radiation, particularly ultraviolet or visible light, either absorption or emission, thermal, volumetric, electrochemically, and the like. Desirably, the signal will be read as electromagnetic radiation in the ultraviolet or visible region, particularly from about 250 to 750 nm.

The temperature at which the signal is observed will generally range from about 10°–50° C., more usually from about 15°–40° C.

Standard assay media can be prepared which have known amounts of analyte. The observed signals with the standard assay media may then be graphed, so as to relate concentration to signal. Once a standard curve has been established, a signal may be directly related to the conentration of the analyte.

After all the materials have been combined, the readings may be made as a rate mode or equilibrium mode. One can normally begin the reading immediately or within about 2 sec. of having completed the additions of the various materials and in a rate mode can take a second reading within 0.2 min, usually 0.5 min. or longer, normally not exceeding an hour, preferably not exceeding 5 min. In an equilibrium mode, one must wait until the mixture has stabilized to a fairly constant reading which can be as little as 0.5 min. and as long as 1 hr. or longer.

Materials

The materials involved in the assay are the analyte (ligand or antiligand), the colloidal particle reagent, which includes the label conjugate and ligand analog conjugate or ligand conjugate, ligand receptor or modified receptor as appropriate, and auxiliary reagents as appropriate.

Analyte

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 1,000,000 molecular weight, more usually from about 20,000 to 600,000 molecular weight; among the hormones of interest, the molecular weights will usually range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:
protamines
histones
albumins
globulins
scleroproteins
phosphoproteins
mucoproteins
chromoproteins
lipoproteins
nucleoproteins
glycoproteins
unclassified proteins, e.g. somatotropin, prolactin, insulin, pepsin A number of proteins found in the human plasma are important clinically and include:
Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
$\alpha_1$-glycoprotein
$\alpha_1$X-Glycoprotein
Thyroxin-binding globulin
Inter-$\alpha$-trypsin-inhibitor
Gc-globulin
  (Gc 1-1)
  (Gc 2-1)
  (Gc 2-2)
Haptoglobin
  (Hp 1-1)
  (Hp 2-1)
  (Hp 2-2)
Ceruloplasmin
Cholinesterase
$\alpha_2$-Lipoprotein(s)
Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G
  (IgG) or $\gamma$G-globulin
Mol. formula:
  $\gamma_2\kappa_2$ or $\gamma_2\lambda_2$
Immunoglobulin A (IgA) or $\gamma$A-globulin
Mol. formula:
  $(\alpha_2\kappa_2)_n$ or $(\alpha_2\lambda_2)_n$
Immunoglobulin M
  (IgM) or $\gamma$M-globulin
Mol. formula:
  $(\mu_2\kappa_2)^5$ or $(\mu_2\lambda_2)^5$ Immunoglobulin D(IgD) or γD-Globulin (γD)
Mol. formula:
 (δ₂κ₂) or (δ₂λ₂)
Immunoglobulin E (IgE) or γE-Globulin (γE)
Mol. formula:
 (ε₂κ₂) or (ε₂λ₂)
Free K and γ light chains
Complement factors:
C'1
 C'1g
 C'1r
 C'1s
C'2
C'3
 β₁A
 α₂D
C'4
C'5
C'6
C'7
C'8
C'9

Important blood clotting factors include:

| BLOOD CLOTTING FACTORS | |
|---|---|
| International designation | Name |
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:

Peptide and Protein Hormones
 Parathyroid hormone
 (parathromone)
 Thyrocalcitonin
 Insulin
 Glucagon
 Relaxin
 Erythropoietin
 Melanotropin
 (melanocyte-stimulating hormone; intermedin)
 Somatotropin
 (growth hormone)
 Corticotropin
 (adrenocorticotropic hormone)
 Thyrotropin
 Follicle-stimulating hormone
 Luteinizing hormone
 (interstitial cell-stimulating hormone)
 Luteomammotropic hormone
 (luteotropin, prolactin)
 Gonadotropin
 (chorionic gonadotropin)
Tissue Hormones
 Secretin
 Gastrin
 Angiotensin I and II -continued
 Bradykinin
 Human placental lactogen
Peptide Hormones from the Neurohypophysis
 Oxytocin
 Vasopressin
 Releasing factors (RF)
 CRF, LRF, TRF, Somatotropin-RF,
 GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
|---|---|
| Streptococcus pyogenes | Polysaccharide |
| Diplococcus pneumoniae | Polysaccharide |
| Neisseria meningitidis | Polysaccharide |
| Neisseria gonorrhoeae | Polysaccharide |
| Corynebacterium diphtheriae | Polysaccharide |
| Actinobacillus mallei, Actinobacillus whitemori | Crude extract |
| Francisella tularensis | Lipopolysaccharide Polysaccharide |
| Pasteurella pestis | |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of cells and tuberculin |
| Klebsiella aerogenes | Polysaccharide |
| Klebsiella cloacae | Polysaccharide |
| Salmonella typhosa | Lipopolysaccharide, Polysaccharide |
| Salmonella typhi-murium, Salmonella derby Salmonella pullorum | Polysaccharide |
| Shigella dysenteriae | Polysaccharide |
| Shigella flexneri | |
| Shigella sonnei | Crude, polysaccharide |
| Rickettsiae | Crude extract |
| Candida albicans | Polysaccharide |
| Entamoeba histolytica | Crude extract |

Other materials of interest include allergens

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids; isoquinoline alkaloids; quinoline alkaloids; which includes quinine and quinidine; diterpene alkaloids, their derivatives and metabolites.

The next group of drugs includes steroids, which includes the estrogens, gestogens, androgens, andrenocortical steroids, bile acids, cardiotonic glycosides and aglycones, which includes digoxin and digoxigenin, saponins and sapogenins, their derivatives and metabolites. Also included are the steroid mimetic substances, such as diethyl stilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, With alkyl of from 2 to 3 carbon atoms, which includes the amphetamines, catecholamines, which includes ephedrine, L-dopa, epinephrine, narceine, papaverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FNM, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

The next group of compounds is amino acids and small peptides which include polyiodothyronines e.g. thyroxine, and triiodothyronine, oxytocin, ACTH, angiotensin, met- and leu-enkephalin their metabolites and derivatives.

Metabolites related to diseased states include spermine, galactose, phenylpyruvic acid, and porphyrin type The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins, IgA, IgG, IgE and IgM, the molecular weights will generally vary from about 160,000 to about $10^6$. Enzymes will normally range from about 10,000 to 600,000 in molecular weight. Natural receptors vary widely, generally being at least about 25,000 molecular weight and may be $10^6$ or higher molecular weight, including such materials as avidin, thyroxine binding globulin, thyroxine binding prealbumin, transcortin, etc.

Ligand Analog-or Ligand-Lipophile Conjugates

The conjugate will vary depending upon the nature of the ligand as well as the lipophile. Either functional groups which are present in the ligand will be employed for linking or the ligand will be modified and functional groups introduced to provide a ligand analog for conjugating to the lipophile.

For the most part, carbonyl functionalities will find use, both oxo carbonyl e.g. aldehyde and non-oxocarbonyl (including nitrogen and sulfur analogs) e.g. carboxy, imidoyl and thionocarboxy.

Alternative functionalities to oxo include active halogen, diazo, mercapto, olefin, particularly activated olefin, amino, phosphoro and the like. A description of linking groups may be found in U.S. Pat. No. 3,817,837, which disclosure is incorporated herein by reference.

The linking groups may vary from a bond to a chain of from 1 to 10, usually from about 1 to 8 atoms, normally carbon, oxygen, sulfur, nitrogen and phosphorous. The number of heteroatoms in the linking group will normally range from about 0 to 6, more usually from about 1 to 4.

For the most part, the linking groups will be aliphatic, although with diazo groups, aromatic groups will usually be involved.

When heteroatoms are present, oxygen will normally be present as oxo or oxy, bonded to carbon, sulfur, phosphorous or hydrogen, nitrogen will normally be present as amino, normally bonded solely to carbon, sulfur or phosphorous; sulfur would be analogous to oxygen; while phosphorous will be bonded to carbon, sulfur, oxygen or nitrogen, usually as phosphonate and phosphate mono- or diester.

Common functionalities in forming a covalent bond between the linking group and the molecule to be conjugated are alkylamine, amide, amidine, thioamide, urea, thiourea, guanidine, diazo, thioether, carboxy and phosphate esters and thioesters.

For the most part, the lipophilic compounds will have a non-oxo carbonyl group, a phosphate group, an amino group, oxy (hydroxyl or the sulfur analog, mercapto) or oxocarbonyl (aldehyde). These functionalities will be linked to amine groups, carboxyl groups, olefins, and active halogen e.g. bromoacetyl. Where an amine and carboxylic acid or its nitrogen derivative or phosphoric acid are linked, amides, amidines and phosphoramides will be formed. Where mercaptan and activated olefin are linked, thioethers will be formed. Where a mercaptan and an active halogen are linked, thioethers will be formed. Where aldehyde and an amine are linked under reducing conditions, an alkylamine will be formed. Where a carboxylic acid or phosphate acid and an alcohol are linked, esters will be formed.

A variety of amphiphilic compounds can be employed as the lipophilic source for conjugation to the ligand. These compounds will have as their polar groups, those functionalities which have been described above.

Other than those compounds which will be described in the section on the amphiphilic compounds for the preparation of the colloidal particles, various compounds can find use for conjugation to the ligand. Illustrative compounds include derivatives of sulfuric acid, phosphoric acid and formic acid, where a hydrogen or hydroxyl group may be replaced with groups bearing one to four lipophilic chains of from 10 to 36 carbon atoms, of which at least 8 carbon atoms are aliphatic (including alicyclic). Illustrative compounds include alkyl sulfates, alkyl benzene sulfonates, alkyl phosphates, alkyl phosphonates, aliphatic carboxylic acids, alkyl phosphonic acids, and the like.

The lipophilic compounds which find use for conjugation to the ligand or label will for the most part have the following formulii:

$(X)_nR(O)_mPO_2OY$
$((X)_nR(O)_mPO_2O)_2Z$
$(X)_nR(O)_mSO_2OM$
$(X)_nR^1SO_2OM$
$(X)_nRCO_2M$ or $(X)_nRC(NH)OM^1$
$(R^2)_pN(H)_rR^3NH_2$
$RCHO$
$RSH$ wherein R is an aliphatic group of from about 10 to 150, usually 12 to 90, more usually 16 to 80 carbon atoms;

R may have a single aliphatic chain of from 8 to 36 carbon atoms, usually 10 to 24 carbon atoms, or a plurality of such chains linked to an alkyl chain of from 2 to 6, usually 2 to 4 carbon atoms, there being from 2 to 6, usually 2 to 4 of such chains linked through an ether, thioether, carboxyester, phosphate ester or amino, particularly an ammonium group, preferably a carboxyester group; R may be saturated or unsaturated having from 0 to 12, usually 0 to 8 sites of ethylenic unsaturation as the only unsaturation, particulary where the aliphatic groups are derived from naturally occurring aliphatic carboxylic acids having from 0 to 3 sites per chain, each site separated by at least one carbon atom;

X is a substituent on R and is amino, hydroxyl; or carboxamido of from 10 to 20 carbon atoms;

$R^1$ is alkylbenzene of from 14 to 30 carbon atoms;

$R^2$ is aliphatic hydrocarbon of from 10 to 30 carbon atoms having from 0 to 3 ethylenic groups;

$R^3$ is alkylene of from 2 to 6 carbon atoms;

M is hydrogen or an alkali metal salt (including ammonium) and $M^1$ is alkyl of from 1 to 6 carbon atoms;

Y is M or a monovalent aliphatic group of from 2 to 10, usually 2 to 6 carbon atoms having at least one heterofunctionality which is hydroxyl, amino, carboxy or aldehyde, generally having not more than 6, usually not more than 4, more usually not more than 2, of such functionalities, and has from 1 to 6 usually 1 to 4, heteroatoms which are oxygen and nitrogen as oxy and amino, or is $(X)_nR$;

Z is an alkylene group of from 2 to 6 carbon atoms having 0 to 1 oxy group;

n is 0 to 2, usually 0 to 1;
m is 0 or 1;
p is 1 to 3; and
r is equal to p−3

The ligand conjugate will for the most part have the following formula:
W-T-ligand
wherein W-T is
$(X)_nR(O)_mPO_2O$
$(X)_nR(O)_mPO_2OY^1$
$(X)_nR(O)_mSO_2O$
$(X)_nR^1SO_2O$
$(X)_nRCO$
$(X)_nRC(NH)$
$(R^2)_pN(H)_rR^3NH$
$R$
$RS$ T is a bond or the nitrogen, oxygen or sulfur which links to the hapten; and $Y^1$ is the same as Y but does not include M The lipophilic compound and the ligand can be conjugated acccording to conventional means which are well known in the literature.

Of particular interest are the conjugates of a naturally occurring lipophilic compound with a fluorescing compound. These compounds will be for the most part of the following formula:

$$ACO_2CH_2CH(O_2CA)CH_2OPO_2^{\ominus}OCH_2CHODFl\ M^{\oplus}$$
$$|$$
$$W$$

wherein the $ACO_2$'s are the same or different and are aliphatic fatty acids of from 12 to 18 carbon atoms;

D is a linking group of from 2 to 8, usually 2 to 4 carbon atoms and may have from 1 to 4 heteroatoms, which are oxygen as oxy, nitrogen as amino, and sulfur as sulfonamido;

M has been defined previously,

Fl is a fluorescer, particularly having an absorption maximum above 400 nm, preferably above 450 nm, and W is hydrogen or $(CH_2OPO_2OCH_2CH(O_2CA)CH_2O_2CA$.

For cardiolipin, W is $-(CH_2OPO_2OCH_2CH(O_2CA)CH_2O_2CA$
wherein the $ACO_2$'s are the same or different and are fatty acids of from 16 to 18 carbon atoms, particularly palmitic and stearic acids. The preferred fluorescer is a fluorescein drivative, linked at the 4 or 5 position of the phenyl group.

Label-Lipophile Conjugate

As previously indicated, a wide variety of labels may be employed. There are only a few primary factors which restrict the choice of label. The first factor is that a signal can be obtained, either directly or indirectly. The second factor is that the signal may be modulated by the proximate presence of a receptor, which receptor may be modified with a molecule which is capable of interacting with the label to modulate the signal. A third factor is that the label can be bound to the liquid particle by virtue of the presence of lipophilic groups, either naturally present or introduced synthetically.

The nature of the detectible signal may be varied widely. The nature of the signal may be as a result of absorption or emission or electromagnetic radiation, preferably light of a wavelength in the range of about 250 to 750 nm, or the signal may be acoustically, thermometrically, volumetrically, or electrochemically detected.

While it is not essential for the subject invention, in order to enhance sensitivity it is desirable that the label provides for a plurality of events per label, rather than a single event. Therefore, while chromogens which absorb light and do not fluoresce could be used, particularly chromogens absorbing at wavelengths higher than 350 nm, for the most part they will not be employed. Rather, chromogens which both absorb and emit light, namely fluorescers, will be preferred.

Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolyphenyl, 2-oxo-3-chromen, indole, xanthene, 7-hydroxycoumarin, phenoxazine, salicylate, strophanthidin, porphyrins, triarylmethanes and flavin.

Individual fluorescent compounds which have functionalities for linking or can be modified to incorporate such functionalities include dansyl chloride, fluoresceins such as 3,6-dihydroxy-9-phenylxanthhydrol, rhodamineisothiocyanate, N-phenyl 1-amino-8-sulfonatonaphthalene, N-phenyl 2-amino-6-sulfonatonaphthalene, 4-acetamido-4-isothiocyanatostilbene-2,2'-disulfonic acid, pyrene-3-sulfonic acid, 2-toluidinonaphthalene-6-sulfonate, N-phenyl, N-methyl 2-aminonaphthalene-6-sulfonate, ethidium bromide, atebrine, auromine-O, 2-(9'-anthroyl)palmitate, dansyl phosphatidylethanolamine, N,N'-dioctadecyl oxacarbocyanine, N,N'-dihexyl oxacarbocyanine, merocyanine, 4-(3'-pyrenyl)butyrate, d-3-amino-desoxyequilenin, 12-(9'-anthroyl)stearate, 2-methylanthracene, 9-vinylanthracene, 2,2'-(vinylene-p-phenylene)bis-benzoxazole, p-bis[2-(4-methyl-5-phenyloxazolyl)]benzene, 6-dimethylamino-1,2-benzophenazin, retinol, bis(3'-aminopyridinium) 1,10-decandiyl diiodide, sulfonaphthyl hydrazone of hellebrigenin, chlortetracycline, N-(7-dimethylamino-4-methyl-2-oxo-3-chromenyl) maleimide, N-[p-(2-benzimidazoyl)phenyl] maleimide, N-(4-fluoranthyl) maleimide, bis(homovanillic acid), reazarin, 4-chloro-7-nitro-2.1.3-benzooxadiazole, merocyanine 540, resorufin, rose bengal, and 2,4-diphenyl-3(2H)-furanone.

The fluorescing chromogen will preferably absorb light at wavelengths longer than 350 nm, preferably longer than 400 nm, and particularly preferred longer than 450 nm. The extinction coefficient is preferably greater than $10^4$ above 400 nm, preferably greater than $10^4$ above 450 nm and more preferably greater than $10^5$ above 400 nm. Preferably, the fluorescer emits light above 400 nm, more preferably above 450 nm.

It should be noted that the absorption and emission characteristics of the dye may vary from being free in solution and being bound to a colloidal particle. Therefore, when referring to the various wavelength ranges and characteristics of the dyes, it is intended to indicate the dyes as employed and not the dye which is unconjugated and characterized in an arbitrary solvent.

An alternative source of light as a detectible signal is a chemiluminescent source. The chemiluminescent source involves a compound which becomes electronically excited by a chemical reaction and may then emit light which serves as the detectible signal or donates energy to a fluorescent acceptor.

The chemiluminescent source may have a single component or a plurality of components, usually two or three components. The chemiluminescent source may be divided into two categories: those which do not involve the intermediacy of enzyme catalysis; and those which do involve enzyme catalysis.

Considering chemiluminescent sources which do not involve enzyme catalysis, only those sources can be employed which chemiluminesce under conditions which do not interfere with the other reactions or interactions involved in the assay. While ordinarily, chemiluminescent sources which are dependent on nonaqueous solvents and strong basic conditions, greater than pH11, will not be useful, techniques can be employed involving rapid injections or flow techniques where the modulated emission is substantially completed before the protein is denatured and significant dissociation occurs. After injection of base, one would observe a burst of light, which could be measured.

A diverse number of families of compounds have been found to provide chemiluminescence under a variety of conditions. One family of compounds is 2,3-dihydro-1,4-phthalazinediones. The most popular compound is luminol, which is the 5-amino compound. Other members of the family include the 5-amino-6,7,8-trimethoxy and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents.

The next group of chemiluminescent compounds are indolen-3-yl hydroperoxides, precursors thereto and derivatives thereof.

The next group of compounds is the bis-9,9'-biacridinium salts, of which lucigenin, N,N'-dimethyl-9,9'-biacridinium dinitrate is illustrative. These compounds chemiluminesce upon combination with alkaline hydrogen peroxide.

The next group of compounds is acridinium salts which are substituted in the 9 position. Particular substituents are carboxylic esters, particularly the aryl esters, acyl substituents, particularly benzoyl, and cyano. Alkaline hydrogen peroxide is employed to induce chemiluminescence.

Another group of compounds is various acyl peroxy esters and hydroperoxides, which may be formed in situ, in combination with compounds such as 9,10-diphenylanthracene.

Another source of chemiluminescence is hydroperoxides e.g. tetralin hydroperoxide, in combination with metal complexes, particularly porphyrins and phthalocyanines, where the metals are iron and zinc.

Preferred systems are those which provide a satisfactory quantum efficiency of emission from the chemiluminescer at a pH at or below 11, preferably at or below 10, and, furthermore, rely on a catalyst which may be conjugated to a member of the specific binding pair or are prevented from undergoing a chemiluminescent reaction by binding of antilabel.

The next group of compounds is based on chemiluminescers which chemiluminesce under enzymatic catalysis. Primarily, there are two groups of enzymatically catalyzed chemiluminescers. The first group is those compounds which chemiluminesce in combination with alkaline hydrogen peroxide. By employing a peroxidase e.g. horse radish peroxidase, in combination with hydrogen peroxide and the chemiluminescer, chemiluminescence can be achieved. Illustrative systems include 2,3-dihydro-1,4-phthalazinediones.

The second enzymatic source of chemiluminescence is based on luciferins and their analogs and luciferases. Of particular importance are bacterial luciferases.

The next group of labels concern catalysis, both enzymatic and non-enzymatic catalysis. A wide variety of non-enzymatic catalysts are described in U.S. patent application Ser. No. 815,636, the appropriate portions of which are incorporated herein by reference. As illustrative of electron transfer agents, which can accept and donate both 1 and 2 electrons are alizarin, 1,2-naphthoquinone, chloranil, 2,6-dichloro- and 2,6-dibromophenolindophenol, flavin, riboflavin, galactoflavin, lumiflavin, pyocyanine, neutral red, safranine, phenazine methosulfate, methylviologen, benzylviologen, Wurster's blue, metal complexes, such as porphyrins, phthalocyanines and phenanthrolines, dihydropyridines, such as NADH, Hanztsch ester and benzyl-1,4-dihydronicotinamide, methylene blue and Meldola blue.

Among enzymatic catalysts, a wide variety of enzymes may be employed. The considerations in choosing an enzyme label may be found in U.S. Pat. No. 3,817,837, the appropriate portions of which are incorporated herein by reference.

Of particular interest are those enzymes set forth in the following table, in accordance with the I.U.B. classification.

1. Oxidoreductases
  1.1 Acting on the CH—OH group of donors
    1.1.1 With NAD or NADP as acceptor
      1. alcohol dehydrogenase
      6. glycerol dehydrogenase
      26. glyoxylate reductase
      27. L-lactate dehydrogenase
      37. malate dehydrogenase
      49. glucose 6-phosphate dehydrogenase
      17. mannitol 1-phosphate dehydrogenase
    1.1.2 With cytochrome as an acceptor
      3. L-lactate dehydrogenase
    1.1.3 With $O_2$ as acceptor
      4. glucose oxidase
      9. galactose oxidase
  1.2 Acting on the CH—$NH_2$ group of donors
    1.43 With $O_2$ as acceptor
      2. L-amino acid oxidase
      3. D-amino acid oxidase
  1.6 Acting on reduced NAD or NADP as donor
    1.6.99 With other acceptors
      diaphorase
  1.10 Acting on diphenols and related substances as donors
    1.10.3 With $O_2$ as acceptor
      1. polyphenol oxidase
      3. ascorbate oxidase
  1.11 Acting on $H_2O_2$ as acceptors
    1.11.1
      6. catalase
      7. peroxidase
3. Hydrolases
  3.1 Acting on ester bonds
    3.1.1 Carboxylic ester hydrolases
      7. cholinesterase
    3.1.3 Phosphoric monoester hydrolases
      1. alkaline phosphatase
    3.1.4 Phosphoric diester hydrolases
      3. phospholipase C
  3.2 Acting on glycosyl compounds
    3.2.1 Glycoside hydrolases
      1. α-amylase
      4. cellulase
      17. lysozyme
      23. β-galactosidase
      27. amyloglucosidase
      31. β-glucuronidase
  3.4 Acting on peptide bonds
    3.4.2 Peptidyl-amino acid hydrolase
      1. carboxypeptidase A
    3.4.4 Peptidyl-peptide hydrolase
      5. α-chymotrypsin
      10. papain
  3.5 Acting on C—N bonds other than peptide bonds
    3.5.1 In linear amides
      5. urease
  3.6 Acting on acid anhydride bonds
    3.6.1 In phosphoryl-containing anhydrides
      1. inorganic pyrophosphatase
4. Lyases
  4.1 Carbon-carbon lyases
    4.1.2 Aldehyde lyases
      7. aldolase
  4.2 Carbon-oxygen lyases
    4.2.1 Hydrolases
      1. carbonic anhydrase -continued 4.3 Carbon-nitrogen lyases
    4.3.1 Ammonia lyases
      3. histidase A further label involves a compound having an enzymatically labile bond. By cleavage of the bond, a product is produced which provides, either directly or indirectly, a detectible signal. The cleavage of the labile bond can result in a compound which is freed from the lipophilic group or is retained with the lipophile. In either event, the resulting product is transformed from an inactive compound unable to provide the detectible signal to an active compound which is capable of providing a detectible signal.

Illustrative of such situations are chemiluminescers and fluorescers, which on being substituted at a functionality which affects the chromogenic properties of the chromogen, do not emit light until the substituent is enzymatically removed. By bonding a substituent to the label by an enzymatically labile bond, the bond can be enzymatically broken so as to produce the chromogen in active form. In one modification, the compound is bound to the lipophilic group by an enzymatically labile bond and is a coenzyme which is then released into the solution in active form, and by appropriate choice of enzymes, may be recycled repetitively to produce a compound providing a detectible signal e.g. NAD or NADP. An extension discussion of this type of technique may be found in co-pending application Ser. No. 751,504, filed Dec. 17, 1976 and German Offenlenungsschriften Nos. 2,618,419 and 2,618,511, both filed April 28, 1975 by Bogulaski et al.

Lipophilic Group

The lipophilic group will normally have one to six straight or branched chain aliphatic groups of at least 6 carbon atoms, more usually at least 10 carbon atoms, and preferably at least 12 carbon atoms, usually, not more than 36 carbon atoms, more usually not more than 30 carbon atoms. The aliphatic group will normally be terminal and may be bonded to rings of from 5 to 6 members, which may be alicyclic, heterocyclic, or aromatic. The compounds which are employed for conjugation can be simple aliphatic compounds having a polar group, which may be a single functionality or a complex group of functionalities at one end of the hydrocarbon chain. The polar group can be an acyl group, particularly carboxy and phosphoryl esters, an hydroxylic group, which may be employed for forming an ether or ester link, an amino group, which may serve to provide an alkylamino, an amide, amidine, or urea link, or a mercaptan, which may serve to form a thioether group with an activated olefin.

Of particular interest for conjugation are the amphiphilic compounds, particularly phospholipids. The phospholipids are based upon aliphatic carboxylic acid esters of aliphatic polyols, where at least one hydroxylic group is substituted with a carboxylic acid ester of from about 8 to 36, more usually of from about 10 to 20 carbon atoms, which may have from 0 to 3, more usually from 0 to 1 site of ethylenic saturation and at least 1, normally only 1 hydroxyl group substituted with phosphate to form a phosphate ester. The phosphate group may be further substituted with small aliphatic compounds which are of di or higher functionality, generally having hydroxyl or amino groups.

The following is a list of amphiphilic compounds which may be conjugated to labels or ligands to prepare the conjugate: phosphatidyl ethanolamine, phosphatidyl choline, phosphatidyl serine, dimyristoylphosphatidyl choline, egg phosphatidyl choline, dipalmitoylphosphatidyl choline, phosphatidic acid, cardiolipin, lecithin, galactocerebroside, sphingomyelin, dicetylphosphate, phosphatidyl inositol, 2-trihexadecylammoniumethylamine, 1,3-bis(octadecyl phosphate)-2-propanol, stearoyloxyethylene phosphate, etc.

Other compounds which may be employed include cholesterol, sitosterol, strophanthidin, ergosterol, and the like.

Other compounds may also be used which have lipophilic groups and which have been described previously. For the most part, these compounds will be alkylbenzenes, having alkyl groups of from 6 to 20 carbon atoms, usually mixtures of alkyl groups, which may be straight or branched chain, and having a carboxyl group, an hydroxylic group, a polyoxy alkylene group (alkylene of from 2 to 3 carbon atoms), carboxylic group, sulfonic acid group, or amino group. Aliphatic fatty acids may be used which will normally be of from about 10 to 36, more usually of from about 12 to 20 carbon atoms. Also, fatty alcohols having the carbon limits indicated for the fatty acids, fatty amines of similar carbon limitations and various steroids may also find use.

The primary consideration is that the lipophilic group is capable of strongly binding to the colloidal particle, so that substantially all or all of the label and ligand are bound to colloidal particles, rather than being free in solution.

Receptor

The receptors are generally relatively large molecules which are capable of specifically recognizing a spatial and polar organization and capable of binding preferentially to such organization. The receptors may be naturally occurring, may be produced by inducing an immunological response to an antigen, or may be obtained synthetically. For the most part, the receptors will be naturally occurring or produced by inducing immunological response so that antibodies are obtained.

Receptors include such molecules as antibodies, Fab fragments, enzymes, naturally occurring receptors, such as avidin, thyroxine binding globulin, thyroxine binding prealbumin, and the like. However, since naturally occurring receptors are for the most part limited to a relatively narrow group of compounds, and rarely can be used to bind to synthetic compounds, for the most part antibodies or Fab fragments will be employed.

Depending upon the nature of the assay, the receptor (antiligand) may be employed without modification or may be conjugated to a compound which interacts with the label in order to provide the modulation of the detectible signal.

Where the label produces light, either by fluorescence or chemiluminescence, a chromogen may be conjugated to the receptor which absorbs light in the wavelength range emitted by the label. This can be as a result of contact, but is more normally a result of dipole-dipole interaction which can occur over a distance as far as about 70 Å. Normally, the receptor will have at least one chromogen and generally not more than one chromogen per 1,000 molecular weight of the receptor, more usually not more than one chromogen per 1,500 molecular weight of the receptor.

For a further description of the interaction of two chromogens, see U.S. Pat. No. 3,996,345 and co-pending application Ser. No. 893,910, filed Apr. 5, 1978.

A second modification of the receptor may be by conjugation with enzymes. In this situation, the enzyme label produces a product which is either the substrate of the enzyme conjugated to the receptor or interacts with the product of the enzyme conjugated to the receptor. An extensive discussion of the use of two enzymes which provides a detectible signal by directly or indirectly interacting may be found in co-pending application Ser. No. 893,650, filed Apr. 4, 1978.

Furthermore, combinations of the above method may be employed, where the enzyme is the label and a chromogen is employed which is conjugated to the receptor. Particularly, an enzyme can be employed which reacts with a compound to produce a chemiluminescent product which can then interact with the chromogen bound to the receptor to transfer energy to the chromogen. An extensive discussion of this technique may also be found in co-pending application Ser. No. 893,650, referred to above.

Colloidal Particles

The liquid particles may be formed from either compounds which are solely lipophilic, that is, have no or only a minor heterofunctionality, that is, have from one to two groups, which under the conditions of the assay exist primarily in neutral form e.g. oxy, carboxyester, phosphate esters and amino, or amphiphilic, where the compounds have at least one polar group which under the conditions of the assay exist in the ionic form e.g. carboxylate, sulfonate, phosphate, ammonium, or sulfonium.

For the most part, the colloidal particles will be vesicles or liposomes having at least 16 mole percent, more usually at least 60, and usually not more than 99.5, more usually not more than about 95 mole percent of phospholipid. Various phospholipid compounds can be employed which have been described previously.

The vesicles or liposomes are made in accordance with conventional techniques as described in U.S. Pat. No. 3,850,578, Humphries and McConnell, supra, Uemura and Kinsky (1972), Biochemistry 11, 485 and Six, et al (1973) Biochemistry 12, 403.

The oil particles can be made in accordance with conventional procedures by combining the appropriate lipophilic compounds with a surfactant, anionic, cationic or nonionic, where the surfactant is present in from about 0.1 to 5, more usually from about 0.1 to 2 weight percent of the mixture and subjecting the mixture in an aqueous medium to agitation, such as sonication or vortexing. Illustrative lipophilic compounds include hydrocarbon oils, alkyl phthalates, trialkyl phosphates, etc.

The ligand and label conjugates to the lipophilic compounds may be incorporated into the liquid particles either prior to, during or after the preparation of the liquid particles. Each of the conjugates will normally be present in from about 0.05 to 15, more usually 0.05 to 10, frequently from about 0.05 to 5 and preferably from about 0.1 to 5 mole percent of the molecules present on the surface of the colloidal particle. For vesicles or liposomes, generally there will be at least about 0.5 mole percent, more usually at least about 1 mole percent of each of the conjugates. Depending on the nature of the label, for vesicles or liposomes, about 0.05 to 15, usually from about 0.1 to 5 mole percent of the total moles of amphiphiles employed for preparing the liposome will be the label conjugate.

Various techniques for synthesizing labeled liposomes are well known. The techniques can involve covalent bonding or noncovalent bonding, depending upon the nature of the ligand and or label. Furthermore, depending upon the nature of the ligand and/or label, individual lipophilic compounds or combinations of lipophilic compounds may be preferred. In certain situations, an amphiphilic compound may be preferred which has a positive charge or a negative charge or is neutral. In addition, the particular compounds may be preferably combined with other lipophilic compounds of the same or different charge. Therefore, no generalizations can be made, but with each combination of ligand and label, it will frequently be desirable to employ one or a combination of lipophilic compounds to enhance the sensitivity of the assay. The particular combination can provide more stable structures for the vesicle, enhance binding of the receptor to the ligand, or provide for greater changes in the signal or response with variation in concentration of the analyte.

Desirably, vesicles will have from about 1 to 50, usually 2 to 40 mole percent of a steroid, particularly a cholestanol derivative e.g. cholesterol.

Kits

In order to provide enhanced sensitivity and accuracy, the materials employed in the assay may be provided as kits. That is, the materials are prepared in predetermined ratios to enhance the response with variation in concentration of the analyte over the range of interest.

The kit will normally include the colloidal particle reagent dispersed in an aqueous medium, usually buffered to a pH in the range of 5 to 10. The concentration of the particles will generally range from about $5 \times 10^{-6}$ to 5 weight percent, usually $5 \times 10^{-4}$ to 1 weight percent. When ligand is the analyte, antiligand will be included in the kit. Where a modified antiligand is employed, it will be included regardless of the nature of the analyte. Usually, the antiligand is provided as lyophilized powder, with or without a bulking agent.

In addition, any auxiliary reagents required for the determination of the signal may be included. Also, other reagents, such as buffers, salts, preservatives, stabilizers and the like may be combined with one or more of the materials.

The following examples are offered by way of illustration and not by way of limitation.

EXPERIMENTAL

All temperatures not otherwise indicated are in centrigrade. All percents and parts not otherwise indicated are by weight, except when two liquids are combined, and the percents are by volume. The following abbreviations are employed: DMF-dimethylformamide; PC-phosphatidyl choline; CL-cardiolipin; PE-phosphatidyl ethanolamine; DPPE-dipalmitolyl phosphatidyl ethanolamine.

EXAMPLE 1

Cardiolipin hemisuccinate

In ~25 ml ethanol-free chloroform was dissolved 100 mg of cardiolipin. The solution was saturated with succinic anhydride (~2 g) and refluxed under $N_2$ for 24 hrs. At the end of this time, the mixture was cooled, filtered and the solvent evaporated. The residue was taken up in 20 ml pet. ether, filtered and the solvent evaporated; this procedure was then repeated with 5 ml pet. ether. The product showed a single spot (Rf=0.64) on TLC using $CHCl_3$, 6.5 µl/MeOH 3.5 µl/conc. $NH_4OH$, 6 drops. Purification of this material on two preparative TLC plates gave a wax-like residue, homogeneous by TLC, which had an IR absorption at 1590 cm$^{-1}$, indicating the presence of a carboxylate anion.

EXAMPLE 2

Conjugate of cardiolipin and fluorescein

In 20 ml of dry benzene was combined 100 µl oxalyl chloride and 50 mg cardiolipin hemisuccinate. After stirring for 0.5 hr under nitrogen at room temperature, infra-red analysis showed the presence of unreacted starting material and the acid chloride (absorption at 1795 cm$^{-1}$) an additional 100 µl of oxalyl chloride was added and the reaction continued for 0.5 hr. The ratio of acid chloride to free acid was unchanged, estimated to be about 3:1. After stripping the solvent in vacuo, 20 ml of benzene was added, the solvent stripped again, and the residue evacuated for 1 hr.

To the above residue was added a 3:1 benzene-dry DMF solution containing 50 mg fluoresceinamine and the mixture was stirred at room temperature over the weekend. The solvent was removed in vacuo and the residue dissolved in ~5 ml chloroform. The reaction mixture was analyzed by TLC using $CHCl_3$, 6.5 µl/MeOH, 3.5 µl/conc. $NH_4OH$, 6 drops as eluent. The main product was highly fluorescent and had Rf=0.61. Other components identifiable were the starting materials, cardiolipin hemisuccinate (Rf=0.64) and fluoresceinamine (Rf 0.3., streak). The crude mixture was applied to eight preparative TLC plates and developed with the solvent component above. The band at Rf=0.6 was separated and extracted from the silica with MeOH and dried under vacuum to yield a fluorescent waxlike material. Analytical TLC showed a brightly fluorescent spot at Rf=0.6 followed by a faint fluorescent spot at Rf=0.44. This second spot was still present when the main spot was repeatedly isolated and rechromatographed, and seems therefore to be a decomposition product caused by the chromatographic conditions. The 60 mHz nmr spectrum showed the presence of the fatty acid and aromatic protons. The I.R. showed an ester absorption at 1740 cm$^{-1}$. The ultraviolet spectrum of an ca. $1.6 \times 10^{-6}$ molar solution in methanol, 50%/0.05 M phosphate buffer, pH 8, 50%, gave a $\gamma_{max}$ of 485 nm.

EXAMPLE 3

Conjugate of phenobarbital and dipalmitoyl phosphatidyl ethanolamine (DPPE)

In 10 ml dry benzene was combined 26.6 mg 5-phenyl-5-(3'-carboxyallyl)barbituric acid and 63.5 mg oxalyl chloride. After refluxing for 2 hrs, 10 ml additional benzene was added and refluxing continued for 1.5 hr. The mixture was evaporated to dryness and the residue washed with benzene.

To the residue was added 20 ml dry $HCCl_3$ and 88.9 mg DPPE and the mixture refluxed for ~3 hr, at which time it was evaporated to dryness and redissolved in $HCCl_3$. The material was then purified by TLC with 65:35:4 $CHCl_3$:MeOH:conc.$NH_4OH$ as eluent.

The 60 mHz nmr gave a ratio of aromatic to aliphatic protons of 0.08 (except 0.07). The IR in $CHCl_3$ showed a prominent ester absorbance at 1740 cm$^{-1}$ and the presence of an amide absorbance at 1680 cm$^{-1}$. The TLC gave a single spot with no ninhydrin reactive material present.

EXAMPLE 4

Conjugate of dipalmitoyl phosphatidyl ethanolamine and fluorescein

The procedure of Uemura et al, (1974) Biochemistry 13, 1972 was employed.

Into 5 ml of a 100 μM solution of triethanolamine in methanol was dissolved 34.7 mg DPPE and 38.8 mg fluoresceinisothiocyanate, the mixture purged with argon, the flask sealed, and the mixture allowed to stand overnight. Chloroform (20–25 ml) was then added to bring everything into solution and the mixture stirred for 20 hrs at room temperature. The mixture was then concentrated to about 10 ml by flash evaporation.

The product was then purified using TLC with HCCl$_3$:MeOH:H$_2$O (70:30:5) as eluent in scintered glass funnels using low vacuum. After drying the plate, it was washed with MeOH and the product dissolved in HCCl$_3$:MeOH(2:1).

The material was homogeneous on TLC (Rf=0.76). No ninhydrin reactive material remained.

In order to demonstrate the subject invention, a number of assays were carried out. The first assay concerns the determination of phenobarbital antibodies, followed by an assay for the determination of phenobarbital.

The liposomes for the assay were prepared as follows: as solutions, 3.25 μmol PC in CHCl$_3$, 0.165 μmol phenobarbital conjugate with phosphatidyl ethanolamine in MeOH and 0.0162 μmol of cardiolipin-fluorescein conjugate in CHCl$_3$ were combined, the solvents evaporated, 5 ml of 0.1 M tris-HCl pH 8 added and the mixture sonicated for 3 min on a Branson sonifier with microtip, power setting of 2.5 at 30°. For use in the assay, the liposome solution was diluted 55-fold.

The protocol for the assay for phenobarbital antibodies is as follows: 50 μl of the liposome solution is combined with 100 μl of a buffer solution (0.1 M Tris-HCl, pH=8.0) followed by the addition of 50 μl of an antiphenobarbital solution diluted with 100 μl of buffer. The mixture was incubated for 15 min, followed by the addition of 50 μl of antifluorescein diluted with 250 μl of buffer, and the resulting assay mixture aspirated directly into a fluorometer interfaced with a HP Autograf model 7000A and a HP9815A desk calculator. The results were read with a 3 sec delay and a 30 sec read time. Where the antiphenobarbital solution was substituted by buffer, the changes in fluorescence (ΔF) based on a least squares program were −9.99; −9.14. Where the antiphenobarbital was employed, the results were −134.13; −142.20; −145.97. Therefore, the presence of antiphenobarbital results in a substantial change in the rate of quenching by anti-fluorescein.

To demonstrate an assay for phenobarbital, a 10 mM solution of phenobarbital in 0.1 M tris-HCl, pH=8 was employed. The protocol for this assay was as follows: 50 μl of the liposome solution was diluted with 100 μl of buffer, followed by the addition of 10 μl of the phenobarbital solution and the mixture incubated for 10 min. To the mixture was then added 50 μl of antiphenobarbital diluted with 100 μl of buffer, followed by a 15 min incubation. Then 50 μl of antifluorescein diluted with 250 μl of buffer was added and the procedure described above followed. With the phenobarbital present, the results were −10.31; −12.24. Where the phenobarbital solution was replaced with a tris solution, the results were −128.69; −133.68. Thus, the presence of phenobarbital results in a substantial reduction in the observed ΔF readings.

The basis for the subject assay is that antifluorescein quenches the fluorescence of the fluorescein. The approach of antifluorescein to the fluorescein is inhibited by the presence of antiphenobarbital bound to the phenobarbital. Therefore, in the first study, when no antiphenobarbital is added, a substantial quenching of the fluorescence is observed. However, in the presence of antiphenobarbital, there is observed a substantial reduction of the quenching of the fluorescence.

In the second study, in the absence of phenobarbital, the antiphenobarbital is able to bind to the phenobarbital in the liposomes, preventing the antifluorescein from binding to the fluorescein in the liposomes. However, when the antiphenobarbital is combined with phenobarbitol, the antiphenobarbital binds to the phenobarbital and is no longer available to bind to the phenobarbital present in the liposomes. Therefore, what is observed is the result as if there was no antiphenobarbital present.

By employing solutions having known amounts of antiphenobarbital or phenobarbital, ΔF/concentration curves could be developed which could then be employed for relating a particular result to a concentration.

The next study was concerned with the determination of anticardiolipin, which is diagnostic for syphilis.

The liposomes were prepared as follows:

A solution of phosphatidyl choline in CHCl$_3$ (3.25 μmol) was combined with a solution of the cardiolipin-fluorescein conjugate in CHCl$_3$ (0.162 μmol) and the solvents evaporated. To the residue was added 5 ml of a 0.1 M tris-HCl solution, pH 8.0, the mixture sonicated for 3 min on a Branson sonifier fitted with a microtip, power setting 2.5, at 30°. The liposome solution was then diluted ten-fold with buffer (0.1 M tris-HCl, pH 8.0).

The protocol was as follows:

A serum sample (50 μl) from a human patient previously determined to have syphilis was combined with 10 μl of the liposome solution described above and the mixture incubated for 10 min, followed by the addition of 250 μl of buffer. To the mixture was then added 25 μl of antifluorescein diluted with 250 μl of buffer and the mixture aspirated immediately into a fluorimeter interfaced with an X-Y plotter and a calculator as described perviously. A 15 sec delay, 30 sec read was employed. Employing a least squares program, the ΔF in the absence of anticardiolipin was: −8.71; −8.62. In the presence of samples having anticardiolipin, the results were: −76.56; −72.45; −84.49. Thus, the presence of anticardiolipin in a serum sample is readily detected and syphilis can be rapidly and accurately diagnosed.

The next assay is for anticardiolipin. Liposomes were prepared by combining chloroform solutions of phosphatidyl choline (24.4 μl, 3.25 μmol), cardiolipin (70 μl, 0.162 μmol) and a methanol solution of phosphatidylethanolamine-fluorescein conjugate (2.5 μl, 0.0162 μmol) and the solvents evaporated. To the mixture was added 5 ml of 0.1 M tris-HCl, pH 8, and the solution sonicated for 3 min. on a Branson sonifier fitted with a microtip, power setting 2.5 at 30° C.

The anticardiolipin was isolated from human specimens. The buffer was 0.1 M tris-HCl, pH 8.0. The protocol was to combine materials in the following order:

50 μl sample, 10 μl liposomes, incubate for 10 min, 250 μl buffer, 25 μl antifluorescein in 250 μl buffer and aspirate the mixture into the fluorimeter with the recorder on. The following results were obtained, measuring the ΔF directly from the graphs between 74 and 220 seconds with anticardiolipin, −10.0, −11.0, −10.0; without anticardiolipin, −3.0, −1.2, −3.0.

The above results demonstrate that one can readily determine anticardiolipin by a simple rapid technique.

It is evident from the above results, that a sensitive assay is provided for the precise determination of a wide variety of compounds. The subject assay employs a unique nucleus for bringing together in relatively close spatial proximity a label and a ligand. This unique nucleus is a colloidal particle which is composed of small organic molecules which allow for binding of the label and the ligand by non-covalent bonds. Furthermore, ligands and labels can be conveniently modified by the same or similar synthetic techniques to provide lipophilic groups for binding the ligand or the label to the colloidal particle. The colloidal particle can be a homogeneous particle comprised of primarily lipophilic compounds surrounded by an amphiphilic surface layer or a membrane enclosing a volume of solution, where the membrane is formed of amphiphilic compounds.

Furthermore, the invention provides new compounds involving the linking of a lipophilic group to a variety of synthetic or naturally occurring drugs or other physiologically active compounds, which do not naturally have lipophilic groups or, while lipophilic, it is preferable to conjugate them to a lipophilic or amphiphilic group. By appropriate conjugation the resulting product is capable of being recognized by the appropriate antibody in competition with the ligand and remains bound to the colloidal particle while also bound to the antiligand.

Although the foregoing invention has been described in some detail by way of illustration and example for purposes of clarity of understanding, it will be obvious that certain changes and modifications may be practiced within the scope of the appended claims.

What is claimed is:

1. In an immunoassay for the determination of an analyte, where the analyte is a member of a specific binding pair consisting of ligand and antiligand and wherein a label is employed which provides a detectible signal, the value of which is affected by the proximity of said antiligand to said label due to the presence of the bulk of said antiligand or a compound conjugated to said antiligand which interacts with said label,
wherein said immunoassay comprises combining in an aqueous medium: (1) a sample suspected of containing said analyte, (2) a reagent comprising ligand or ligand analog and label, wherein said ligand analog is capable of specific binding to said antiligand, and (3) antiligand, when ligand is the analyte or said antiligand is conjugated with said compound which interacts with said label; and
determining the value of said detectible signal as compared to said value determined with a sample having a known amount of analyte;
the improvement which comprises employing as said reagent discrete colloidal particles comprised of a major portion of lipophilic compounds and a minor portion of label and ligand or ligand analog, wherein said label is covalently conjugated to at least one of said lipophilic compounds, and the ligand or ligand analog are lipophilic or made so by conjunction to a lipophilic compound.

2. A method according to claim 1, wherein said lipophilic compound is amphiphilic.

3. A method according to claim 2, wherein said amphiphilic compound is a phosphatidyl compound.

4. A method according to claim 1, wherein said label is a fluorescent compound.

5. A method according to claim 4, wherein said fluorescent compound is conjugated to a phosphatidyl group.

6. A method according to claim 5, wherein said ligand is cardiolipin and said analyte is anticardiolipin.

7. An immunoassay for the determination of an analyte, wherein the analyte is a member of a specific binding pair consisting of ligand and antiligand and wherein a label is employed which provides a detectible signal, the value of which is affected by the proximity of said antiligand to said label due to the presence of the bulk of said antiligand or a compound conjugated to said antiligand which interacts with said label, and
wherein a reagent is employed having both label and ligand or a ligand analog, where ligand analog is capable of specifically binding to said antiligand, said reagent comprising a liposome of amphiphilic molecules having from about 0.05 to 15 mole percent of ligand or ligand analog conjugated to an amphiphile and from 0.05 to 15 mole percent of a label conjugated to at least one of said amphiphile molecules;
wherein said immunoassay comprises combining in an aqueous medium at a pH in the range of about 5 to 10 and at a temperature in the range of about 10° to 50° C.:
a sample suspected of containing said analyte;
said reagent;
and antiligand, when ligand is the analyte or said antiligand is conjugated with a compound which interacts with said label; and
determining the value of said detectible signal as compared to said value determined with a sample having a known amount of analyte.

8. A method according to claim 7, wherein said label is a fluorescer and antifluorescer is added to said medium.

9. A method according to claim 8, wherein said fluorescer is a fluorescein derivative.

10. A method according to any of claims 7 to 9, wherein said ligand is cardiolipin.

11. A method according to claim 7, where from about 16 to 99.5 mole percent of said liposome is phospholipid.

12. A method according to claim 11, where up to 40 mole percent is a cholestanol derivative.

13. An immunoassay for the determination of the presence of anticardiolipin in human serum which comprises:
combining in an aqueous buffered medium at a pH in the range of about 6.5 to 9.5:
(1) a human serum sample suspected of containing anticardiolipin
(2) liposomes comprised of from about 60 to 99.5 mole percent of a phosphatidyl compound, from about 0.05 to 5 mole percent of cardiolipin and from about 0.1 to 10 mole percent of a phosphatidyl-fluorescein conjugate; and
(3) antifluorescein; and
determining the amount of fluorescence from said assay medium as compared to the amount of fluorescence obtained from an assay medium having a known amount of anticardiolipin.

14. An immunoassay composition of matter comprising a liposome having from 16 to 99.5 mole percent of phospholipid, up to 40 mole percent of cholestanol, from about 0.05 to 15 mole percent of a fluorescent label bonded to a phospholipid, wherein said fluorescent label has an extinction coefficient of at least about $10^4$ or at above 350 nm and a hapten of from about 125 to 2,000 molecular weight bonded to at least one phospholipid.

15. An immunoassay composition of matter according to claim 14, wherein said fluorescent label is a fluorescein derivative.

16. An immunoassay composition of matter having at least about 16 mole percent of phospholipid, up to 40 mole percent of a cholestanol, from 0.05 to 15 mole percent of a fluorescent label bonded to a phospholipid and from about 0.05 to 15 mole percent of cardiolipin.

17. An immunoassay composition of matter comprising a liposome having from about 60 to 99.5 mole percent of a phospholipid, from about 0.05 to 5 mole percent of cardiolipin, and from about 0.1 to 10 mole percent of phosphatidyl-fluorescer conjugate.

* * * * *